United States Patent
Pressman

(10) Patent No.: US 6,207,848 B1
(45) Date of Patent: *Mar. 27, 2001

(54) PROCESS FOR THE PRODUCTION OF DIARYL CARBONATES

(75) Inventor: Eric James Pressman, East Greenbush, NY (US)

(73) Assignee: General Electric Company, Schenectady, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/215,388

(22) Filed: Dec. 18, 1998

(51) Int. Cl.⁷ .................................................. C07C 68/00
(52) U.S. Cl. ...................... 558/274; 558/271; 558/272; 558/273
(58) Field of Search ............................................. 558/274

(56) References Cited

U.S. PATENT DOCUMENTS

| | | |
|---|---|---|
| 4,096,169 | 6/1978 | Chalk . |
| 4,187,242 | 2/1980 | Chalk . |
| 4,201,721 | 5/1980 | Hallgren . |
| 5,142,086 | 8/1992 | King, Jr. et al. . |
| 5,284,964 | 2/1994 | Pressman et al. . |
| 5,498,789 | 3/1996 | Takagi et al. . |
| 5,821,377 | * 10/1998 | Buysch et al. ....................... 558/274 |

FOREIGN PATENT DOCUMENTS

| | | |
|---|---|---|
| 0 350 697 A2 | 1/1990 | (EP) . |
| 0 350 697 A3 | 1/1990 | (EP) . |
| 350697 | 1/1990 | (EP) . |
| 350700 | 1/1990 | (EP) . |
| 0 858 991 A1 | 8/1998 | (EP) . |

* cited by examiner

*Primary Examiner*—Michael G. Ambrose
(74) *Attorney, Agent, or Firm*—Noreen C. Johnson; Douglas E. Stoner

(57) ABSTRACT

The method of the present invention comprises reaction of a gaseous mixture of oxygen and carbon monoxide with an aromatic hydroxy compound in the presence of a catalyst under controlled pressure, wherein the partial pressure of oxygen is optimized to effect increased yields at reduced overall pressure.

17 Claims, No Drawings

PROCESS FOR THE PRODUCTION OF DIARYL CARBONATES

BACKGROUND OF THE INVENTION

The present invention relates to the preparation of diaryl carbonates. More particularly, this invention relates to improved methods for the preparation of diaryl carbonates by carbonylation of an aromatic hydroxy compound in the presence of a catalyst.

Diaryl carbonates are valuable monomer precursors for the preparation of polycarbonates by melt transesterification. One route for the synthesis of diaryl carbonates is the direct carbonylation of aryl compounds in the presence of carbon monoxide, oxygen, and a catalyst system. The stoichiometric reaction was discovered in the mid 1970's and is detailed in U.S. Pat. Nos. 4,096,169 and 4,187,242 to A. J. Chalk, which use methylene chloride as a solvent. Subsequent work focused on making the reaction catalytic in palladium, as well as solventless. See, e.g., T. C.-T. Chang, European Patent Application Nos. 350,697 and 350,700.

Use of a multi-component catalyst "package", or system further realized increases in reaction rates. U.S. Pat. No. 4,187,242 to A. J. Chalk, for example, discloses a catalyst system comprising a Group VIIIB element (ruthenium, rhodium, palladium, osmium, iridium and platinum) or complexes thereof, and a co-catalyst selected from Group IIIA, IVA, VA, VIA, IB, IIB, VIB, or VIIB metals, together with a base. Copper is a preferred co-catalyst. U.S. Pat. No. 4,201,721 discloses a catalyst package comprising palladium, a manganese or cobalt complex, a base and a desiccating agent.

Alternative catalyst systems are disclosed, for example, in U.S. Pat. No. 5,142,086 to King, Jr. et al. comprising palladium, a quaternary ammonium salt, a metallic co-catalyst selected from cobalt, iron, cerium, manganese, molybdenum, samarium, vanadium, chromium, and copper, and an organic co-catalyst selected from aromatic ketones, aliphatic ketones, and aromatic polycyclic hydrocarbons. Further improvements to catalyst systems are disclosed in U.S. Pat. No. 5,284,964 to E. J. Pressman, et al. As disclosed therein, improved carbonylation yields are obtained with a catalyst system comprising palladium or palladium complexes, an inorganic co-catalyst selected from cobalt, manganese, and copper salts or complexes, an organic co-catalyst selected from certain heterocyclic amines, such as terpyridines, phenanthrolines, quinolines, and isoquinolines, and quaternary ammonium or phosphonium halides.

U.S. Pat. No. 5,498,789 to Takagi discloses a recent development in catalyst systems, wherein the system comprises palladium, at least one lead compound soluble in a liquid phase, at least one halide selected from quaternary ammonium halides and quaternary phosphonium halides, and optionally at least one copper compound. Use of a lead co-catalyst suppresses the production of aryl aromatic ortho-hydroxycarboxylates as by-products. Suitable lead compounds include lead oxides, for example PbO, $Pb_3O_4$, and $PbO_2$; lead carboxylates, for example $Pb(OCOCH_3)_2$, $Pb(OCOCH_3)_4$, $Pb(C_2O_4)$, and $Pb(OCOC_2H_5)_2$; inorganic lead salts such as $Pb(NO_3)_2$ and $PbSO_4$; alkoxy and aryloxy lead salts such as $Pb(OCH_3)_2$, and $Pb(OC_6H_5)_2$; and lead complexes such as phthalocyanine lead. All of the foregoing patents and disclosures are incorporated by reference herein.

As mentioned above, recent research directed toward improving the direct oxidative carbonylation of aryl compounds to yield diaryl carbonates has focused primarily on the catalyst system. Attempts to reduce the cost of commercially implementing direct carbonylation has furthermore focused almost exclusively on three areas: minimizing the cost of the catalyst system components; increasing the efficiency of the catalyst system; and efficient reclamation and recycling of the various catalytic components. In accordance with European Patent Application Nos. 350,697 and 350,700 to T.C.-T. Chang, U.S. Pat. No. 4,096,168 to Haligren, U.S. Pat. No. 5,231,210 to Joyce et al, and U.S. Pat. No. 5,284,964, above, an optimized catalyst system requires a palladium source (presently palladium acetate), an inorganic co-catalyst (cobalt di-(salicylal)-3,3'-diamino-N-methyldipropylamine, hereinafter CoSMDPT), an organic co-catalyst (presently 2,2':6',2"-terpyridine), and a bromide source (generally a tetraalkylammonium bromide or hexaalkylguanidinium bromide). The catalyst system is stirred in neat phenol at 100 to 200 ° C. while a gaseous carbon monoxide and oxygen mixture of constant composition is introduced at elevated pressure (up to 1600 pounds per square inch).

However, numerous other variables can also affect the cost of carbonylation of aromatic compounds on a commercial scale, including reaction pressure. U.S. Pat. No. 5,399,734 to King, Jr. et al. discloses that reaction at elevated pressure is required to provide commercially acceptable rates and selectivities. King et al. discloses that improved yields are achieved by a mixture of carbon monoxide and oxygen in the reactor at a substantially constant molar ratio and partial pressure. The mixture of carbon monoxide and oxygen comprises from 2 to 50 mole % of oxygen (based on total carbon monoxide and oxygen), and is introduced into the reactor until a pressure of 200 to 3500 pounds per square inch (psi) at 25° C. is reached. The Examples disclose use of 7.1 mole % of oxygen in carbon monoxide, at total pressures of 2800 psi.

Despite the advantages of this approach, maintaining the reaction at increased total pressure, e.g., up to 3500 psi, substantially increases the installed investment cost for carbonylation on commercial scales. Advances which permit the operation of this process at reduced total pressure without deleteriously affecting diaryl carbonate production rate and selectivity are therefore clearly desirable.

SUMMARY OF THE INVENTION

The above-described and other disadvantages of the prior art are overcome or alleviated by the improved method of the present invention comprising producing diaryl carbonates by reacting, in the presence of an effective amount of a catalyst system, an aromatic hydroxy compound with carbon monoxide and oxygen under controlled pressure, wherein the partial pressure of oxygen is optimized to effect comparable yields at reduced overall pressure. More particularly, the improved method described herein comprises producing diaryl carbonates by reacting an aromatic hydroxy compound, in the presence of an effective amount of a catalyst system, with carbon monoxide and oxygen under a controlled total pressure, wherein the molar ratio and partial pressure of the oxygen are optimized to effect increased carbonylation of the aromatic hydroxy compound at a total pressure which is reduced compared to the total pressure required to achieve similar yields under non-optimized molar ratios and partial pressures of oxygen.

DETAILED DESCRIPTION OF THE INVENTION

Commercial-scale carbonylation of aromatic hydroxy compounds is ordinarily conducted at high total pressures, up to about 3500 psi. These pressures are required in order to produce about one mole of diaryl carbonate per liter-hour, the reaction rate estimated to be economically feasible. The present method allows a significant reduction in the total reaction pressure, from 3500 pounds per square inch (246.07 kg/cm$^2$) to about 1600 pounds per square inch (112.5 kg/cm$^2$), or to about 1000 pounds per square inch (70.31 kg/cm$^2$) or even lower, while maintaining this target diaryl carbonate production rate. Optimization of the partial pressure of oxygen allows comparable yields at total pressures of less than about 3500 psi, preferably less than or equal to about 1600 psi, even more preferably less than or equal to about 1000 psi, 800 psi, or 500 psi.

The invention is illustrated by the data shown in the Table below, wherein optimization of the partial pressure of oxygen at 1600 psi, 800 psi and 500 psi results in reaction rates comparable to those achieved at 1600 psi or higher. Reactions are run in accordance with the Example detailed below.

TABLE 1

| Run No. | Reaction Pressure (psi) | Percent of O$_2$ in Feed* | Reaction Rate** (2 Hours) |
| --- | --- | --- | --- |
| A | 500 | 6.53 | 0.55 |
| B | 500 | 6.87 | 0.64 |
| C | 500 | 7.54 | 0.83 |
| D | 500 | 9.42 | 0.92 |
| E | 500 | 12.58 | 0.49 |
| F | 800 | 4.38 | 0.54 |
| G | 800 | 5.15 | 0.78 |
| H | 800 | 6.43 | 0.95 |
| I | 800 | 7.00 | 0.98 |
| J | 800 | 7.15 | 0.97 |
| K | 800 | 9.51 | 1.18 |
| L | 800 | 11.46 | 1.05 |
| M | 1600 | 7.24 | 1.09 |
| N | 1600 | 7.63 | 1.22 |
| O | 1600 | 8.15 | 1.22 |
| P | 1600 | 8.18 | 1.06 |
| Q | 1600 | 11.70 | 0.91 |

*Balance of gas feed is carbon monoxide
**Rate = moles of diphenyl carbonate per liter hour (Assumes density of the reaction mixture is 1.07 grams per milliliter)

The Table indicates that diphenyl carbonate production at reduced total pressure may be achieved by increasing the oxygen partial pressure. Thus, the rate of diphenyl carbonate production at 1600 psi total pressure using 7.24% oxygen in carbon monoxide is exceeded at 800 psi total pressure using 9.51% oxygen in carbon monoxide. In turn, the rate of diphenyl carbonate production at 800 psi total pressure using 5.15% oxygen in carbon monoxide is exceeded at 500 psi total pressure using 7.54% oxygen in carbon monoxide (based on total carbon monoxide and oxygen).

While increasing the partial pressure of oxygen generally results in an increase in reaction rate, unexpectedly, the effect is not constant. Instead the inventors hereof have found that there exists optimum oxygen partial pressures at each total pressure. Oxygen partial pressures may be optimized at particular total reaction pressures according to the Table above. In preferred embodiments, for example, based on total carbon monoxide and oxygen, the oxygen is present in an amount of about 8 molar % to about 10 molar % at a total pressure of about 500 psi, and preferably in an amount of about 9 molar % to about 10 molar % at a total pressure of about 500 psi. Alternatively, the oxygen is present in an amount of about 6 molar % to about 12 molar % (based on total carbon monoxide and oxygen) at a total pressure of about 800 psi, and preferably in an amount of about 6 molar % to about 10 molar % (based on total carbon monoxide and oxygen) at a total pressure of about 800 psi. Preferred amounts of oxygen (based on total carbon monoxide and oxygen) at about 1600 psi are in the range from about 7 molar % to about 10 molar %, and preferably from about 7.5 molar % to about 8 molar %. Optimal quantities of oxygen at other pressures are now readily determinable based on the invention disclosed herein and the above Table.

Carbon monoxide usable in the present invention may be high-purity carbon monoxide or carbon monoxide diluted with another gas such as nitrogen, argon, carbon dioxide or hydrogen, which have no negative effects on the reaction. The oxygen used in the present invention may be high purity oxygen, air, or oxygen diluted with another gas such as nitrogen, argon, carbon dioxide or hydrogen which have no negative effects on the reaction. Preferably, oxygen and carbon monoxide alone are used.

Other components of the reaction include an aromatic hydroxy compound, and a catalyst system. Suitable aromatic hydroxy compounds include monocyclic, polycyclic or fused polycyclic aromatic monohydroxy or polyhydroxy compounds having from 6 to 30, and preferably from 6 to 15 carbon atoms. Illustrative aromatic compounds include, but are not limited to, phenol, cresol, xylenol, resorcinol, hydroquinone, naphthol, catechol, cumenol, the various isomers of dihydroxynaphthalene, bis(4-hydroxyphenyl)propane-2,2,$\alpha$,$\alpha$'-bis(4-hydroxyphenyl)p-diisopropylbenzene, and bisphenol A. Aromatic organic monohydroxy compounds are particularly preferred, with phenol being the most preferred.

A broad variety of catalyst systems known in the art are suitable in the practice of the present invention. Exemplary catalyst systems include those disclosed in U.S. Pat. No. 4,096,168 to Haligren, e.g., a catalyst selected from the group consisting of Group VIIIB metal catalysts, e.g., ruthenium, rhodium, palladium, osmium, iridium, or platinum having an oxidation state of plus one, in the form of a complex or an oxide, halide, nitrate, sulfate, or organic salt, and an organic base such as an amine; and in European Patent Application Nos. 350,697 and 350,700 to T.C.-T. Chang, which further discloses use of a cobalt (II) or divalent or trivalent manganese halide or carboxylate salt or amine, diketone, or carbon monoxide complex, and a quinone, such a 1,4-benzoquinone and hydroquinone. Preferred catalyst systems are disclosed in U.S. Pat. No. 5,231,210 to Joyce et al, describing a palladium catalyst in combination with a quaternary ammonium or phosphonium halide and a cobalt (II) salt complexed with a pentadentate ligand selected from the group consisting of aromatic amines, aliphatic amines, aromatic ethers, aliphatic ethers, aromatic or aliphatic amine ethers, and Schiff bases.

A preferred catalyst system comprises at least one palladium source, at least one inorganic co-catalyst, at least one halide source, optionally at least one organic co-catalyst, and an optional desiccant. Examples of suitable palladium or palladium compounds include palladium black; supported palladium such as palladium/carbon, palladium/alumina, palladium/silica and the like; inorganic palladium salts such as palladium chloride, palladium bromide, palladium iodide, palladium sulfate, palladium nitrate and the like; and organic palladium salts such as palladium acetate, palladium oxalate and the like. Palladium (II) acetylacetonate, (Pd(acac)$_2$), palladium complexes such as PdCl$_2$(PhCN)$_2$, PdCl$_2$(PPh$_3$)$_2$, and others known in the art, or a mixture of palladium and a compound which can produce the above complexes in the reaction system may also be used. Palladium/carbon, palladium acetate, and Pd(acac)$_2$ are preferred. An effective amount of the palladium catalyst is, for example, an amount sufficient to provide about 1 mole (gram-atom) of palladium per 100 to 10,000,000 and preferably per 1000 to 1,000,000 equivalents of aromatic hydroxy compound.

At least one inorganic co-catalyst is also present in the catalyst system. Preferred inorganic co-catalysts include divalent or trivalent manganese halide or carboxylate salts, or amine, diketone, or carbon monoxide complexes; or cobalt (II) halide or carboxylate salts, or amine, diketone, or carbon monoxide complexes, e.g., cobalt chloride and cobalt acetate. Also useful are cobalt (II) salts complexed with a pentadentate ligand selected from the group consisting of aromatic amines such as bipyridines, pyridines, terpyridines, quinolines, isoquinolines, and biquinolines; aliphatic amines such as ethylene diamine and tetraalkylethylenediamines, such as tetramethylethylenediamine; aromatic ethers, such as crown ethers; aliphatic ethers; aromatic or aliphatic amine ethers such as cryptands; and Schiff bases, such as di-(salicylal)-3,3'-diamino-N-methyldipropylamine. An effective amount of inorganic co-catalyst is an amount sufficient to provide from about 0.1 to about 5.0, and preferably from about 0.5 to about 1.5 mole of metal per mole of palladium.

At least one organic co-catalyst may optionally be present in the catalyst system. Organic co-catalysts, when present, include, for example, quinones and aromatic diols formed by the reduction of said quinones, or a mixture thereof. 1,4-Benzoquinone and hydroquinone have been found to be effective, as well as compounds such as 1,2-quinone and catechol, anthraquinone, 9,10-dihydroxy anthracene, and phenanthraquinone. Aromatic organic amines are preferred, for example terpyridines, phenanthrolines, and quinolines such as 2,2':6'2"-terpyridine, 2,2':6',2"-4-thiomethylterpyridine, 2,2':6',2"-terpyridine-N-oxide, 1,10-phenanthrolines, 2,4,7,8-tetramethyl-1,10-phenanthroline, 4,7-diphenyl-1,10-phenanthroline, and 3,4,7,8-tetramethyl-1,10-phenanthroline. An effective amount of organic co-catalyst is an amount sufficient to provide from about 0.1 to about 3.0, and preferably from about 0.3 to about 1.0 mole of organic co-catalyst per mole of palladium.

At least one halide source is also present in the catalyst system. The halide source is preferably a quaternary ammonium halide or quaternary phosphonium halide represented by the following formula:

$R_1R_2R_3R_4NX$ or $R_1R_2R_3R_4PX$ wherein $R_1$ to $R_4$ are each independently an alkyl group or aryl group, each group independently having a carbon number of 1 to about 24, and X is halogen. Bromides are preferred, for example tetra-n-butylammonium bromide, tetraphenylphosphonium bromide and the like. Other halide sources include hexaalkylguanidinium halides, particularly hexaalkylguanidinium chlorides or bromides. Hexaethylguanidinium bromide is preferred. Mixtures of halide sources may be used. An effective amount of halide source is an amount sufficient to provide from about 5 to about 150, and preferably from about 20 to about 50 moles of halide per mole of palladium.

The optional desiccant in the present invention is preferably at least one material such as a molecular sieve. 3 Angstrom (A) molecular sieves are presently preferred. The presence of a desiccant is particularly important over long reaction times, for example in continuous reaction processes, in order to prevent degradation of the diaryl carbonate product. The presence of a desiccant such as 3A molecular sieves can lead to increases in the palladium turnover number, which can provide a significant economic savings for a large-scale process.

An inert solvent such as hexane, heptane, cyclohexane, benzene, toluene, xylene, methylene chloride, chloroform, chlorobenzene, diethyl ether, diphenyl ether, tetrahydrofuran, dioxane or acetonitrile can be used. When an aromatic hydroxy compound as a raw material is used as a reaction solvent, an additional solvent need not be used, although mixtures of solvents are also suitable for use in the present invention.

The described aromatic hydroxy compound and catalyst system are charged under the optimized partial pressure of oxygen and carbon monoxide and preferably heated. Reaction temperatures in the range of about 60–150° C. are typical. In order for the reaction to be as rapid as possible, it is preferred to substantially maintain the total gas pressure and partial pressure of carbon monoxide and oxygen, as is described herein, until conversion of the hydroxy aromatic compound is complete.

The diaryl carbonates produced by the method of this invention may be isolated by conventional techniques. It is often preferred to form and thermally crack an adduct of the diaryl carbonate with the hydroxy aromatic compound, as is described in U.S. Pat. Nos. 5,239,106 and 5,312,955.

The following Example is provided by way of example only, and should not be read to limit the scope of the invention.

Catalyst system activity was studied using a constant composition gas flow reactor system as disclosed in the aforementioned U.S. Pat. No. 5,399,734. To the reactor at room temperature were added phenol (60.63 grams, 644 millimoles), tetrabutylammonium bromide (2.082 gram, 6.46 millimoles), cobalt di-(salicylal)-3,3'-diamino-N-methylidipropylamine (CoSMDPT, 0.126 grams, 0.307 millimoles), 2,2':6'2"-terpyridine (0.0250 grams, 0.107 millimoles), and palladium acetate (Pd(OAc)$_2$, 0.0636 grams, 0.283 millimoles). Molecular sieves (⅛ inch pellets, 3A, 37 grams) were placed in a perforated Teflon basket mounted to the stir shaft of the reactor. The reactor vessel was sealed. While heating to 110° C. over 10 minutes, a specified percent of oxygen in carbon monoxide gas was bubbled at a flow rate of 350 milliliters per minute through the reactor contents, which were maintained at 780–820 pounds per square inch. Gas flow at the aforementioned composition, rate, and pressure was continued for 2 hours while maintaining the reaction mixture at 110° C. At this time an aliquot was removed from the reaction and analyzed by High Performance Liquid Chromatography (HPLC) in order to determine the yield of diphenyl carbonate. Results are reported in the aforementioned Table. At an oxygen partial pressure of 9.51%, the yield was 46.5 wt %, and the phenol selectivity to diphenyl carbonate was 96%.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method for the production of diaryl carbonates, said method comprising reacting an aromatic hydroxy compound, in the presence of an effective amount of a catalyst system comprising:
   at least one palladium source, and
   at least one inorganic co-catalyst which is a cobalt(II) halide or carboxylate salt or amine, diketone or carbon monoxide complex or a cobalt(II) salt complexed with a pentadentate ligand selected from the group consisting of aromatic amines, aliphatic amines, aromatic ethers and Schiff bases;

with a gas mixture comprising carbon monoxide and oxygen under an applied total pressure, wherein the mole percentage of oxygen in said gas mixture is as follows:

between about 8 and about 10 mole percent at a total pressure less than or equal to about 500 pounds per square inch, between about 6 and about 12 mole percent at a total pressure above about 500 and less than or equal to about 800 pounds per square inch, or between about 7 and about 10 mole percent at a total pressure above about 800 and less than or equal to about 1600 pounds per square inch.

2. The method of claim 1, wherein the oxygen is present in an amount of about 9 to about 10 molar % based on total oxygen and carbon monoxide at a total pressure of about 500 psi.

3. The method of claim 1, wherein the oxygen is present in an amount of about 6 to about 10 molar % based on total oxygen and carbon monoxide at a total pressure of about 800 psi.

4. The method of claim 1, wherein the oxygen is present in an amount of about 7.5 to about 8 molar % based on oxygen and carbon monoxide at a total pressure of about 1600 psi.

5. The method of claim 1, wherein the catalyst system further comprises a halide source.

6. The method of claim 5, wherein the Group VIIIB metal catalyst is at least one of palladium or a palladium compound selected from the group consisting of inorganic palladium salts, organic palladium salts, and palladium complexes.

7. The method of claim 6, wherein the Group VIIIB metal catalyst is a palladium compound selected from the group consisting of palladium chloride, palladium bromide, palladium iodide, palladium sulfate, palladium nitrate, palladium acetate, palladium oxalate, palladium (II) acetylacetonate, $PdCl_2(PhCN)_2$, and $PdCl_2(PPh_3)_2$.

8. The method of claim 5, wherein the inorganic co-catalyst is cobalt di-(salicylal)-3,3'-diamino-N methyl-dipropylamine.

9. The method of claim 5, wherein the halide source is at least one member selected from the group consisting of quaternary ammonium halides represented by the formula $R_1R_2R_3R_4NX$ wherein $R_1$ to $R_4$ are each independently an alkyl group or aryl group, each group independently having a carbon number of 1 to about 24, and X is a halide; quaternary phosphonium halides represented by the formula $R_1R_2R_3R_4PX$ wherein $R_1$ to $R_4$ are each independently an alkyl group or aryl group, each group independently having a carbon number of 1 to about 24, and X is a halide; hexaalkylguanidinium halides; tetra-n-butylammonium bromide, tetraphenylphosphonium bromide, and hexaethylguanidinium bromide.

10. The method of claim 9, wherein the halide source is selected from the group consisting of tetra-n-butylammonium bromide, tetraphenylphosphonium bromide, and hexaethylguanidinium bromide.

11. The method of claim 5, wherein the optional organic co-catalyst is at least one member selected from the group consisting of quinones, 1,4-benzoquinone, hydroquinone, 1,2-quinone, catechol, anthraquinone, 9,10-dihydroxy anthracene, phenanthraquinone, aromatic organic amines, terpyridines, phenanthrolines, quinolines, 2,2':6'2"-terpyridine, 2,2':6',2"-4-thiomethylterpyridine, 2,2':6',2"-terpyridine-N-oxide, 1,10-phenanthrolines, 2,4,7,8-tetramethyl-1,10-phenanthroline, 4,7-diphenyl-1,10-phenanthroline, and 3,4,7,8-tetramethyl-1,10-phenanthroline.

12. The method of claim 11, wherein the optional organic co-catalyst is selected from the group consisting of 1,4-benzoquinone, hydroquinone, catechol, anthraquinone, 9,10-dihydroxy anthracene, and 2,2':6'2"-terpyridine.

13. The method of claim 5, wherein there is also present a desiccant.

14. The method of claim 5, wherein the palladium compound is palladium acetate, the halide source is tetra-n-butylammonium bromide or hexaethylguanidinium bromide, the inorganic co-catalyst is cobalt di-(salicylal)-3,3'-diamino-N-methyldipropylamine, the organic co-catalyst is 2,2':6',2"-terpyridine, and further comprising 3-Angstrom molecular sieves.

15. The method of claim 1, wherein the aromatic hydroxy compound is selected from the group consisting of monocyclic aromatic monohydroxy compounds, polycyclic aromatic monohydroxy compounds, fused polycyclic aromatic monohydroxy compounds, monocyclic aromatic polyhydroxy compounds, polycyclic aromatic polyhydroxy compounds, fused polycyclic aromatic polyhydroxy compounds, phenol, cresol, xylenol, resorcinol, hydroquinone, naphthol, catechol, cumenol, isomers of dihydroxynaphthalene, bis(4-hydroxyphenyl)propane-2,2, α,α'-bis(4-hydroxyphenyl)p-diisopropylbenzene, and bisphenol A.

16. The method of claim 15, wherein the aromatic hydroxy compound is phenol.

17. A method for the production of diaryl carbonates, said method comprising reacting an aromatic hydroxy compound, in the presence of an effective amount of a catalyst system comprising at least one palladium source and cobalt di-(salicylal)-3,3'-diamino-N-methyldipropylamine, with a gas mixture consisting essentially of carbon monoxide and oxygen under an applied total pressure, wherein the mole percentage of oxygen in said gas mixture is as follows:

about 9–10 mole percent at a total pressure less than or equal to 500 pounds per square inch, about 6–10 mole percent at a total pressure above 500 and less than or equal to 800 pounds per square inch, and about 7.5–8 mole percent at a total pressure above 800 and less than or equal to 1600 pounds per square inch.

* * * * *